United States Patent [19]

Zoumas et al.

[11] Patent Number: 5,849,729
[45] Date of Patent: Dec. 15, 1998

[54] USE OF HYDROLYZED COCOA BUTTER FOR PERCUTANEOUS ABSORPTION

[75] Inventors: Barry L. Zoumas; Stanley M. Tarka, both of Hershey; J. Michael McKim; Bryan J. Simmons, both of Elizabethtown; James G. Marks, Jr., Hershey; Michael Santanna, Harrisburg, all of Pa.

[73] Assignee: Hershey Foods Corporation, Hershey, Pa.

[21] Appl. No.: 578,455

[22] Filed: Dec. 26, 1995

[51] Int. Cl.⁶ .......................... A61K 31/56; A61K 31/07
[52] U.S. Cl. .......................... 514/169; 514/178; 514/725
[58] Field of Search ..................... 514/169, 725, 514/178, 786, 772

[56] References Cited

U.S. PATENT DOCUMENTS

| | | |
|---|---|---|
| 3,609,102 | 9/1971 | Schlossman . |
| 3,654,327 | 4/1972 | Castner . |
| 3,856,936 | 12/1974 | Vick et al. . |
| 3,860,702 | 1/1975 | Buell . |
| 3,862,197 | 1/1975 | Castner . |
| 3,878,297 | 4/1975 | Vick . |
| 4,165,385 | 8/1979 | Lefebvre . |
| 4,450,292 | 5/1984 | Christidis et al. . |
| 4,454,118 | 6/1984 | Johnson . |
| 4,454,159 | 6/1984 | Musher . |
| 4,537,776 | 8/1985 | Cooper . |
| 4,707,354 | 11/1987 | Garlen et al. . |
| 4,784,849 | 11/1988 | Tutsky . |
| 4,828,825 | 5/1989 | Weber et al. . |
| 5,009,969 | 4/1991 | Miller . |
| 5,019,604 | 5/1991 | Lemole . |
| 5,039,516 | 8/1991 | Goodman et al. . |
| 5,045,308 | 9/1991 | Spiegel et al. . |
| 5,057,497 | 10/1991 | Calam et al. . |
| 5,112,613 | 5/1992 | Honda et al. . |
| 5,141,741 | 8/1992 | Ishida et al. . |
| 5,188,831 | 2/1993 | Nicoll et al. . |
| 5,208,012 | 5/1993 | Sudo et al. . |
| 5,216,033 | 6/1993 | Pereira et al. . |
| 5,219,558 | 6/1993 | Woodin, Jr. et al. . |
| 5,223,250 | 6/1993 | Mitchell et al. . |
| 5,229,130 | 7/1993 | Sharma et al. . |
| 5,232,691 | 8/1993 | Lemole . |
| 5,306,486 | 4/1994 | McCook et al. . |
| 5,622,993 | 4/1997 | McGinity et al. ...................... 514/626 |

FOREIGN PATENT DOCUMENTS

| | | |
|---|---|---|
| 61227521A | 10/1986 | Japan . |
| 3169820A | 7/1991 | Japan . |
| 95621 | 9/1988 | Romania . |
| 2007186 | 2/1994 | Russian Federation . |
| 1182463 | 5/1968 | United Kingdom . |
| 2202726 | 10/1988 | United Kingdom . |

OTHER PUBLICATIONS

F–D–C Reports, Acc. No. 2150430009, The Rose Sheet, vol. 15, Iss. 43, Oct. 1994.

Handbook of Chemistry and Physics, 54$^{th}$ edition, CRC Press (Cleveland, OH) Weast (ed.) pp. D–189–90, 1973–1974.

*Primary Examiner*—Raymond Henley, III
*Attorney, Agent, or Firm*—Scully, Scott, Murphy & Presser

[57] ABSTRACT

The present invention relates to a pharmaceutical formulation prepared from medicaments selected from the group consisting of retinoids, corticosteroids, vitamin D or α or β-hydroxy acids admixed with cocoa butter or partially hydrolyzed cocoa butter emulsion.

31 Claims, 3 Drawing Sheets

USE OF HYDROLYZED COCOA BUTTER FOR PERCUTANEOUS ABSORPTION

FIELD OF THE INVENTION

This invention relates to the enhancement as well as the control of epidermal, derma and transdermal penetration of various topically applied pharmacologically active agents utilizing cocoa butter or partially hydrolyzed cocoa butter emulsion.

BACKGROUND OF THE INVENTION

Intravenous infusion, intramuscular injection, buccal, oral, rectal routes are just a few of the methodologies that have been generally adopted for administration of therapeutically active agents, such as retinoids, corticosteroids, α- or β-hydroxy carboxylic acids and vitamin D. When these therapeutically active agents are administered to humans or warm blooded animals by such routes, they enter the circulatory system and produce the desired systemic therapeutic effect. However, it is well-known that the aforementioned methods of administration have certain disadvantages. For example, buccal and rectal administration often produce discomfort and aggravation to the patient. The intravenous and intramuscular routes are not only painful for the patient, but also must be performed by trained individuals. Oral administration, although generally acceptable by the patient, may have the disadvantages of poor absorption of the therapeutic agent from the gastrointestinal tract and/or degradation which may be caused by the acidic medium of the stomach, enzymes in the gastrointestinal tract, interaction with ingested food or by rapid metabolism by the liver through which the drug must pass before it enters the systemic circulation.

Recognizing these disadvantages, many investigators have used the transdermal route to deliver the therapeutically active agent into systemic circulation. Various therapeutic and cosmetic agents are used for the treatment of a number of skin conditions, for example, hydrocortisone for pruritus and erythema in atopic dermatitis, retinoids for photoaging and treatment of acne, etc. However, the skin of human and other warm blooded animals, especially mammals, provides an excellent barrier to the penetration of exogenous chemical substances.

Skin is a structurally complex, relatively thick membrane. Molecules moving from the environment into and through intact skin must first penetrate the stratum corneum and any material on its surface. They must then penetrate the viable epidermis, the papillary dermis, and the capillary walls into the blood stream or lymph channels. To be so absorbed, molecules must overcome a different resistance to penetration in each type of tissue. Transport across the skin membrane is thus a complex phenomenon. However, it is the cells of the stratum corneum which present the primary barrier to absorption of topical compositions or transdermally administered drugs. The stratum corneum is a thin layer of dense, highly keratinized cells approximately 10–15 microns thick over most of the body. It is believed to be the high degree of keratinization within these cells as well as their dense packing which creates in most a substantially impermeable barrier to drug penetration. For the proper treatment of skin disorders for skin diseases or for the absorption of the pharmaceutical agent into the body, it is important that the pharmacologically active agent penetrates the stratum corneum and be made available at appropriate concentrations at the site of action which can be the stratum corneum, the viable epidermis, the epidermis-dermis junction, the dermis itself or all of the aforementioned layers of the skin, depending upon the type of disorder or disease condition.

For example, in certain skin conditions such as ichthyosis, callus or plaque psoriasis, the stratum corneum is thicker and thus can provide a significantly greater barrier to penetration of the drug, thereby reducing its efficacy.

Moreover, recent studies have shown that as people age their skin becomes more resistant to penetration of drugs.

To achieve a consistent supply of therapeutic active ingredient at the site of action, it has been found that the use of a penetration enhancer is essential. Investigators have turned to various enhancing agents, for example, dimethylsulfoxide, dimethylformamide, methyldecylsulfoxide (U.S. Pat. No. 3,527,864), dimethylacetamide (U.S. Pat. No. 3,472,931) and N-alkyl-2-pyrrolidone (U.S. Pat. No. 3,696,516) for topical use as well as systemic delivery of therapeutic active agents. However, the use of the aforementioned penetration enhancers is not without problems. For example, the use of dimethyl sulfoxide causes in animals a foul taste and body odor, burning and erythema on the skin; a reduction in the relucency of the lens cortex and tissue necrosis (Martinadale, *The Extra Pharmacopoeia*, Pages 1461–1463, 27th ed., 1977). Dimethylformamide and methylacetamide also cause a sensation of burning and erythema on the skin. As a result, there exists a need for a novel agent that enhances the absorption of therapeutic agents through the skin and is substantially devoid of the disadvantages and drawbacks that to date have characterized many prior art penetration enhancing agents.

Furthermore, many of the compounds used in topical application have adverse side effects. For example, a side effect of retin-A is that it causes a transient sensation of warmth or mild stinging and even may cause skin irritation, peeling and blistering. This in many ways is a result of the high concentrations of the compound applied and required in present formulations in order for it to be effective. Thus, there exists a need for an enhancing agent that facilitates the absorption of a therapeutic agent through the barrier stratum corneum of the skin to such an extent that it permits greater concentration of the drug to be absorbed through the skin and/or significantly smaller concentrations of the therapeutic agent to be required for efficacy. In addition, the need is for a vehicle for which there are no side effects associated therewith and which minimizes the side effects on the therapeutic agents with which the vehicle is associated.

The present invention accomplishes these goals by utilizing cocoa butter and partially hydrolyzed cocoa butter emulsion as the means for facilitating the absorption of medicaments through the skin. More specifically, the present invention is directed to the use of cocoa butter and/or hydrolyzed cocoa butter emulsion in combination with various drugs, i.e., retinoids, such as accutane and retin-A; steroids, such as corticosteroids and testosterone; α- or β-hydroxycarboxylic acids, such as lactic acid; and vitamin D. Preferably, the cocoa butter or partially hydrolyzed cocoa butter emulsion is admixed with the retinoids, testosterone, corticosteroids, α- or β-hydroxycarboxylic acid or vitamin D prior to administration.

Heretofore, it is known that fully hydrolyzed cocoa butter (U.S. Pat. No. 3,654,327) has the property of carrying a great variety of medicinal agents through or at least deep into the epidermal and sub-dermal tissues. However, this patent does not identify the medicinal agents nor does it teach or suggest that cocoa butter or partially hydrolyzed cocoa butter emulsion can be used to affect the penetration of drugs, especially, the retinoids, corticosteroids, the α or β-hydroxy acid or vitamin D of the present invention. Moreover, unlike fully hydrolyzed cocoa butter, neither cocoa butter nor partially hydrolyzed cocoa butter emulsion degrades upon cooling.

It has been suggested in U.S. Pat. No. 3,860,702 to Buell ("Buell"), U.S. Pat. No. 3,862,197 to Castner ("Castner") and U.S. Pat. No. 3,856,436 to Vick, et al. ("Vick, et al.") that partially hydrolyzed cocoa butter has the ability to penetrate epidermal tissue and carry with it relatively large molecules such as proteolytic enzymes (Buell) or a mixture of whole bee venom and mellitin (Vick, et al.). However, none of these references recognize that cocoa butter itself can be used to affect the penetration of drugs into the skin (epidermis or dermis) or subdermal tissues. Moreover, these references disclose that partially hydrolyzed cocoa butter emulsion can be used to permit certain proteins, e.g., proteolytic enzyme, or bee venom and mellitin to penetrate the epidermis, but these references to not specify any other specific molecules that could penetrate the skin using partially hydrolyzed cocoa butter emulsion or cocoa butter as the vehicle. More specifically, none of the prior art references recognize that cocoa butter or partially hydrolyzed cocoa butter emulsion can be used to permit the penetration of such molecules as retinoids, α- or β-hydroxy acids, steroids, such as corticosteroids and testosterone, and the like or vitamin D through the skin. Nor do they realize the enhanced ability of the cocoa butter or partially hydrolyzed cocoa butter emulsion as described herein, to permit the absorption of these molecules through the skin.

The use of cocoa butter or partially hydrolyzed cocoa butter emulsion admixed with the reagents indicated hereinabove is very effective in enhancing the absorption through the skin of these medicaments. In fact, both vehicles are so effective that they permit a smaller dosage to be applied in order to be efficacious. Furthermore, if the same concentration as normally applied is utilized, then the effect of the drug is greatly increased. In consequence, the present invention does not suffer from the deficiencies associated with the other modes of administration, described hereinabove. Furthermore, utilizing the cocoa butter or partially hydrolyzed cocoa butter emulsion as the penetration enhancer, less drug is required to achieve a certain efficacy. Moreover, if the same quantity of drug is utilized in the present formulation, more drug would be absorbed through the skin and an enhanced efficacy will be achieved. Finally, since more drug is being absorbed through the skin, the side effects of the drugs, especially on the other layer of the skin, if any, are minimized.

The present invention relates to the enhancement as well as the control of epidermal, dermal and transdermal penetration of medicinal agents selected from the group consisting of retinoids, steroids, such as testosterones and corticosteroids, vitamin D, and α or β-hydroxycarboxylic acids which comprises admixing a pharmaceutically effective amount of said medicinal agent with a penetration enhancing amount of cocoa butter or partially hydrolyzed cocoa butter emulsion and applying the resulting product therefrom topically to the skin of warm-blooded animals especially mammals, and in particular humans. The present invention relates to the pharmaceutical composition comprising a pharmaceutically effective amount of said medicinal agent admixed with the penetration enhancing amount of cocoa butter or a partially hydrolyzed cocoa butter emulsion. The present invention is also related to the treatment of various skin disorders which comprises applying the pharmaceutical composition of the present invention on the locus of the skin afflicted with a dermatological disorder.

DETAILED DESCRIPTION OF THE INVENTION

Figure 1:
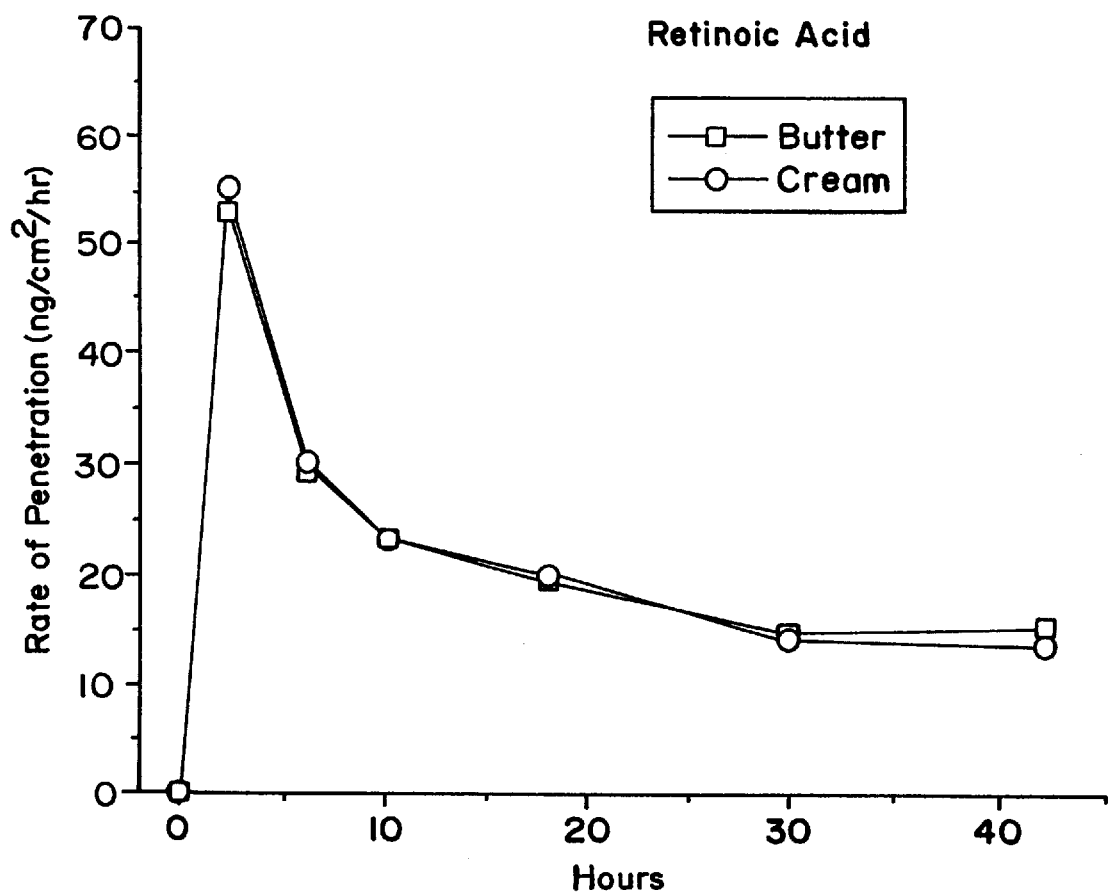
FIG. 1 is a rate profile of the absorption of retinoic acid through a human trunk skin using cocoa butter and partially hydrolyzed cocoa butter emulsion (cream).

By "topical administration" or "topical application" is meant directly laying or spreading upon epidermal tissue, especially outer skin or membrane, including the skin or membrane of the oral or vaginal cavities.

By "safe and effective" is meant a sufficient amount of the permeant composition to provide the desired systemic effect and performance, or local activity, or both at a reasonably benefit/risk ratio attendant any medical treatment. Within the scope of sound medical judgment, the amount of permeant used will vary with the particular condition being treated, the severity of the condition, the duration of the treatment, the specific permeant compound employed, its concentration, the condition of the patient, concurrent therapies being administered and other factors within the knowledge and expertise of the patient or the attending physician or other practitioner.

By "toxicologically- or pharmaceutically-acceptable" is meant the pharmaceutical active (or permeant), and other compatible drugs, medications or inert ingredients which the term describes, are suitable for use in contact with the tissues of humans, mammals and other warm-blooded animals without undue toxicity, irritation, allergic response, and the like commensurate with a reasonable benefit/risk ratio.

By the term "comprising" is meant that various other compatible drugs and medicaments, as well as inert ingredients, occlusive agents, and cosmetic vehicles, can be cojointly employed in the compositions and methods of this invention, as long as the critical penetration enhancement vehicle and pharmaceutically active permeant are used.

By "afflicted situs" is meant a site suitable for topical application with or without the means of a mechanical sustained release device, patch or dressing, e.g. behind the ear, on the arm, back, chest, stomach, leg, top of foot, etc.

By "penetration-enhancing" or "permeation-enhancing" is meant that the penetration enhancing vehicles of this invention with or without optional inert ingredients provide marked transepidermal or percutaneous delivery of an incorporated active permeant, when compared to other compositions, at equal chemical potential. Equal chemical potential is important since varying solubilities of drugs in different carrier vehicles will affect their transport across skin.

As used herein, all percentages and ratios are by weight of the total composition unless otherwise specified.

The terms "permeant", "active", "pharmaceutical active", "pharmacological active", "pharmaceutical agent", "pharmacological agent", "pharmaceutically", or "pharmacologically-active agent", "chemical agent", "therapeutic agent" and "drug" are used interchangeably herein.

The term "retinoids" includes the traditional definition encompassing the natural retinoids, i.e., vitamin A (retinal), vitamin A acid (retinoic acid). However, research has resulted in a much larger class of chemical compounds that are termed retinoids due to their biological similarity to vitamin A and its derivatives. Compounds useful in the present invention include all natural and/or synthetic analogues of vitamin A or retinol-like compounds which possess the biological activity of vitamin A in the skin, such as the control of epithelial cell differentiation of keratinocytes in the epidermis and/or stimulation of fibroplasia or new collagen synthesis in the dermis among other effects. Accordingly, as used herein for purposes of the present invention, the term "retinoid" will be understood to include any of the foregoing compounds. Examples of suitable retinoids for use in the present invention are set forth in Table 1, although it will be understood that the invention is not limited thereto.

TABLE 1

Chemical, Common and/or Commercial Name

Isotretinoin
13-cis-retinoic acid
ACCUTANE

Etretinate
TEGISON
(all-E)-9-(4-methoxy-2,3,6-trimethylphenyl)-3,7-dimethyl-2,4,6,8-nonatetraenoic acid ethyl ester Etretin
(all-E)-9-(4-methoxy-2,3,6-trimethylphenyl)-3,7-dimethyl-2,4,6,8-nonatetraenoic acid Motretinide
N-ethyl-9-(4-methoxy-2,3,6-trimethylphenyl)-3,7-dimethyl-2,4,6,8-nonatetraenamide (E,E)-9-(2,6-dichloro-4-methoxy-3-methylphenyl)-3,7-dimethyl-2,4,6,8-nonatetraenoic acid ethyl ester 7,8-didehydroretinoic acid (E,E)-4-[2-methyl-4-(2,6,6-trimethyl-1-cyclohexen-1-yl)-1,3-butadienyl]benzoic acid retinoic acid
VITAMIN A ACID
TRETINOIN OR RETIN-A (E)-4-[4-methyl-6-(2,6,6-trimethyl-1-cyclohexen-1-yl)-1,3,5-hexatrienyl]benzoic acid (all-E)-3,7-dimethyl-9-(3-thienyl)-2,4,6,8-nonatetraenoic acid (E,E,E)-3-methyl-7-(5,6,7,8-tetrahydro-5,5,8,8-tetramethyl-2-naphthalenyl)-2,4,6-octatrienoic acid (E)-6-[2-(2,6,6-trimethyl-1-cyclohexen-1-yl)ethenyl]-2-naphthalenecarboxylic acid (E,E,E)-7-(2,3-dihydro-1,1,3,3-tetramethyl-1H-inden-5-yl)-3-methyl-2,4,6-octatrienoic acid (E)-4-(2,3-dihydro-1,1,3,3-tetramethyl-1H-inden-5-yl)-1-propenyl]benzoic acid TTNPB
(E)-4-[2-(5,6,7,8-tetrahydro-5,5,8,8-tetramethyl-2-naphthalenyl-2-propenyl]benzoic acid (E)-4-[2-(5,6,7,8-tetrahydro-3-methyl-5,5,8,8-tetramethyl-2-naphthalenyl)-1-propenyl]benzoic acid (E)-1,2,3,4-tetrahydro-1,1,4,4-tetramethyl-6-(1-methyl-2-phenylethyl) naphthalene 6-(1,2,3,4-tetrahydro-1,2,4,4-tetramethyl-6-naphthyl)-2-naphthalene-carboxylic acid (E)-6-[2-[4-(ethylsulfonyl) phenyl-1-methylethenyl]-1,2,3,4-tetrahydro-1,1,4,4-tetramethylnaphthalene 4-[(5,6,7,8-tetrahydro-5,5,8,8-tetramethyl-2-naphthalenyl) ethynyl]benzoic acid (E)-2-(1,1,4,4-tetramethyl-1,2,3,4-tetrahydronaphth-7-yl-[4-tetrazol-5-yl) phenyl]-1-propene (E)-4-[2-(5,6,7,8-tetrahydro-7-hydroxy-5,5,8,8-tetramethyl-2-naphthalenyl)-1-propenyl]benzyl alcohol AM-80
2-(4-carboxybenzamido)-5,6,7,8-tetrahydro-5,5,8,8-tetramethylnaphthalene AM-580
2-[N-4(4-carboxyphenyl)carbamoyl]-5,6,7,8-tetrahydro-5,5,8,8-tetramethyl-naphthalene CH-55
1-[3,5-(Di-tert-butyl)benzoyl]-2-(4-Carboxyphenyl)ethane TTNT
2-(5,6,7,8-tetrahydro-5,5,8,8-tetramethyl-2-naphthyl)-6-benzo(b) thione carboxylic acid TTNF
2-(5,6,7,8-tetrahydro-5,5,8,8-tetramethyl-2-naphthyl)-6-benzo(b) furancarboxylic acid TTNI
2-(5,6,7,8-tetrahydro-5,5,8,8-tetramethyl-2-naphthyl)-6-indole-carboxylic acid TTNN
2-(5,6,7,8-tetrahydro-5,5,8,8-tetramethyl-2-naphthyl)-6-naphthalene carboxylic acid p-(5,6,7,8-tetrahydro-5,5,8,8-tetramethyl-2-anthracenyl) benzoic acid Esters or amides of 13-trans retinoic acid or 13-cis retinoic acid wherein the —OH group of the carboxylic acid (—COOH) group is substituted by —OR$^1$ or NR$^2$R$^3$, wherein R$^1$, R$^2$ and R$^3$ are such that these esters or amides can be converted to 13-trans retinoic acid or 13-cis retinoic acid through hydrolysis, metabolism, cleavage, etc.

Also encompassed within the term "retinoid" are geometric and stereoisomers of the retinoids, e.g., tretinoin (all-trans retinoic acid) and isotretinoin (13-cis-retinoic acid) may also be used. The preferred retinoids are retin-A and isotretinoin (accutane).

The retinoids are substances known to have a broad spectrum of biological activity affecting cell growth, differentiation and proliferation. Retinoids have found clinical utility in the treatment of various dermatological disorders, such as acne, severe cystic acne, psoriasis and other disorders of the keratinization. Other known topical uses include treatment of senile comedones, nervus comedonicus, linear verricous nervus, plantar warts, pseudofolliculitis, keratoacanthoma, solor keratosis of extremities, callosities, keratosis palmaris et plantaris, Darier's disease, ichthyosis, psoriasis, acanthosis nigricans, lichen planus, molluscum contagiosum, reactive perforating collagenosis, melasma, corneal epithelial abrasion, geographic tongue, Fox-Fordyce disease, cutaneous metastatic melanoma and keloids or hypertrophic scars. See U.S. Pat. No. 4,888,342, the contents of which are incorporated by reference.

Retinoids are also useful for treating sundamaged human skin. Caucasians who have had a good deal of sun exposure will show gross cutaneous alterations in adult life, wrinkling, leatheriness, yellowing, looseness, roughness, dryness, mottling, (hyperpigmentation) and various premalignant growths (often subclinical). These changes are most prominent in light-skinned persons who burn easily and tan poorly. The baleful effects of the sun are cumulative, increasing with time often referred to as "photoaging".

Although the anatomic degradation of the skin is most advanced in the elderly, the destructive effects of excessive sun exposure are already evident by the second decade. Serious microtopic alterations of the epidermis and dermis occur decades before these become clinically visible. Wrinkling, yellowing, leatheriness, loss of elasticity, etc. are very late changes.

Retinoids are useful in moderating and preventing the aging changes of the exposed (sun damaged) areas of the skin, especially the face. They retard the effects of photoaging of the skin due to thinning and abnormal differentiation of the epidermis, inter alia. In general, they retard and reverse the loss of collagen fibers, abnormal changes in elastic fibers, deterioration of small blood vessels and formation of abnormal epithelial growths in sundamaged human skin.

More specifically, topical amounts of retinoids in a program of maintenance therapy substantially prevent epithelial neoplasms (basal and squamous cell cancers) and preneoplastic growths (actinic keratoses). The skin significantly regains and maintains its firmness, turgor and elasticity during the therapy. Effacement of fine wrinkles is an important clinical effect. Generally, the maintenance therapy with retinoids is begun in adult life when epithelial growths and other aging changes begin to appear clinically. Pigmentary blotching and mottling are also alleviated.

Retinoids are also useful in the treatment and prophylaxis of cancer.

$\alpha$- or $\beta$-hydroxycarboxylic acid, as used herein, refer to drugs having a hydroxy group on the $\alpha$ or $\beta$ carbon, respectively, to the acyl group in a carboxylic acid which is used to treat psoriasis (dry skin), aging skin, ichthyosis or disturbed keratinization of the skin. The term also includes the salts thereof. Examples thereof include lactic acid, ammonium lactate and the like.

Vitamin D, as used herein, refers to the various vitamin D derivatives, e.g., vitamin D, $D_2$, $D_3$, dihydrotachysterol, calcifediol, calcitriol and the like or derivatives thereof. Vitamin Ds are useful in maintaining calcium homeostasis. They are also useful in treating vitamin D deficiency related diseases and dysfunction of the parathyroid glands. Examples include primary hyperparthyroidism, secondary hyperparathyroidism, hypoparathyroidism, osteomalacia rickets and various dermatological diseases, including eczema, psoriasis and other inflammatory diseases of the skin.

Steroid, as used herein, refers to corticosteroids and testosterones, as defined herein below.

Corticosteroids, as used herein, are glucocorticoid steroids, such as cortisone, hydrocortisone, predisolone, betamethasone and triamcinolone and the like. They are useful, inter alia, in the treatment of collagen-vascular diseases, including rhematoid arthritis, disseminated lupus erythematosus and dermatomyositis. Glucocorticoid steroids are useful in the treatment of Addison's disease, and dermatological diseases, including eczema, psoriasis, and other inflammatory diseases of the skin.

Testosterone, as used herein, includes testosterone, but also derivatives thereof, including but not limited to esters thereof, such as testosterone cypionate, testosterone enanthate, testosterone propionate and the like; methyltestosterone fluoxymesterone, methandrostenolone, oxymetholone, oxandrolone, stanozolol, nandrolone, decanoate, nandrolone phenpropionate, and the like. These are used as androgenic and/or anabolic agents.

There are many maladies which causes testosterone deficiency in men, such as hypogonadism or hypopituitarism. To overcome these deficiencies, androgens, e.g. testosterone, is given to men.

Another use of testosterone, as used herein, is for androgen replacement therapy in men, either at maturity or in adolescence.

The present inventors have surprisingly found that the use of cocoa butter or partially hydrolyzed cocoa butter emulsion admixed with certain medicinal agents increases substantially the rate and/or total absorption of said medicinal agents, i.e., retinoids, $\alpha$- or $\beta$-hydroxycarboxylic acid, vitamin D, testosterone and corticosteroids, through the epidermis of the animal, and are therefore useful in the treatment of various disorders.

Cocoa butter is a term that is readily understood by one skilled in the art, especially the chocolate art. It is the fat obtained by subjecting chocolate liquor to hydraulic pressure. It has been given various definitions by different companies or agencies. As defined by the Federal Drug Administration, it is the edible fat obtained from ground cocoa beans either before or after roasting. U.S. Pharmacopeia defines cocoa butter as the fat obtained from the roasted seed of Theobroma cocoa Linne. The Codex Committee on Cocoa and Chocolate Products defines cocoa butter as the fat produced from one or more of the following: cocoa beans, cocoa ribs, cocoa mass (chocolate liquor), cocoa cake, expeller cake or cocoa dust (fines) by a mechanical process and/or with the aid of "permissible solvents". As used herein, the term cocoa butter incorporates all of these definitions.

Cocoa butter is composed mainly of glycerides of stearic, palmitic, and oleic fatty acids. The triglyceride structure of cocoa butter is about 3% triunsaturated, 22% monounsaturated oleodistearin, 57% oleopalmitostearin, 4% oleodipalmitin, 6% diunsaturated-stereodiolefin, 7% palmitodiolefin and 10% triunsaturated triolein. There are 6 crystalline forms of cocoa butter, but the four basic forms are $\gamma$, $\alpha$, $\beta$ and $\beta^1$. All of these forms of cocoa butter can be used to make the melted cocoa butter or partially hydrolyzed cocoa butter emulsion described herein.

Cocoa butter is prepared by conventional means known to one skilled in the art, especially the chocolate art. A method for its preparation is by subjecting the chocolate liquor to hydraulic pressure. Chocolate liquor, in turn, is prepared by conventional means, such as by the steps of cleaning the cocoa beans, roasting the cocoa bean, winnowing the roasted cocoa bean and grinding the winnowed mass. More specifically, the first step in the process of making cocoa butter is cleaning the cocoa beans and removing the foreign objects therefrom.

The cocoa beans next undergo a roasting step. This is the step wherein chocolate flavor is normally developed. It is essentially a cooking step which promotes reactions of the latent flavor precursors, such as proteins, amino acids and reducing sugars, organic acids and other unidentified compounds in the cocoa bean to form products which are highly flavored. The roasting conditions are adjusted to produce different types of flavor. For example, low, medium or high roasts are produced by varying temperature, humidity and amount of time in the roaster. For instance, a high roast produces strong flavors and dark color, while a low roast produces mild flavors and light color. Roasting temperatures vary from 70° C. to 180° C., while roasting times tend to vary from about 30 to 60 minutes.

Normally, cocoa beans are roasted with the shell still on. However, other variations in the roasting process include nib roasting, wherein the shell is first removed by a rapid or moist heating step, and liquor roasting.

Winnowing, the next step in the process, is the process of separating the nib or kernel from the inedible shell. This is preformed by conventional techniques.

The next step is grinding, wherein the kernel or nib of the cocoa bean is ground. The nib is the cellular mass of the cocoa bean which contains 50–56% cocoa fat. The grinding liberates the fat locked within the cell wall, while producing temperatures as high as 110° C.

The nibs are usually ground while they are still warm after the roasting. The grinding step is accomplished by using conventional techniques. Two modern apparatuses, in particular, are normally used in the grinding step. One uses a pinmill mounted over a roller refiner. The pinmill grinds the nibs to a coarse but fluid liquor. The liquor is delivered to a roll refiner that reduces the particle size until fine. The second type is a vertical horizontal ball mill. In this apparatus, coarsely ground nib is fed to the base of the vertical cylinder that contains small balls in separate compartments. A central spindle causes the balls to rotate at high speeds, grinding the liquor between them and against the internal wall of the cylinder.

As a result of the processes described hereinabove, chocolate liquor is obtained. The cocoa butter is obtained from the chocolate liquor by subjecting the chocolate liquor to hydraulic pressure utilizing procedures known to one skilled in the art. The cocoa butter obtained by this process in known as prime pure cocoa butter.

There are other processes that are used to prepare cocoa butter. For example, expeller cocoa butter is prepared by the expeller process. In this process, cocoa butter is obtained directly from the whole bean by pressing the bean in a cage press. Expeller butter usually has a stronger flavor and darker color than prime cocoa butter and is filtered with carbon or otherwise treated prior to use. Another process for obtaining cocoa butter is a solvent-extracted cocoa butter which is obtained from beans, nibs, liquor cakes or fines by solvent extraction usually with an organic non-polar solvent such as hexane. Refined cocoa butter is any one of the above cocoa butters that have been treated to remove impurities and undesirable odors and flavors.

Any one of the cocoa butters described hereinabove can be utilized to make the melted cocoa butter used in the present invention, or as explained hereinbelow, can be utilized to prepare the partially hydrolyzed cocoa butter emulsion.

Cocoa butter is a solid at room temperature (20° C.) and starts to soften around 30° C. and melts completely just below body temperature. Before cocoa butter is to be used as a penetration enhancer and admixed with an active ingredient, the cocoa butter is first melted. This is accomplished by techniques known in the art, such as by placing cocoa butter in water that has been heated to temperatures ranging from 100° F. to 212° F. for a time sufficient until the cocoa butter melts. It is in this melted state that the cocoa butter is mixed with active ingredients, such as retinoids, and the like. In this melted state, the cocoa butter is comprised of 97–99% triglycerides, about 0.3–0.5% diglycerides, about 0.14% monoglycerides and about 0.5–2% free fatty acid.

Alternatively, the cocoa butter may be used to make partially hydrolyzed cocoa butter.

"Partially hydrolyzed cocoa butter", as used herein, contains cocoa butter that has undergone partial hydrolysis or contains cocoa butter mixed with fully hydrolyed cocoa butter or contains fully hydrolyzed cocoa butter mixed with cocoa butter having partial hydrolysis of the triglycerides or combination thereof. As described hereinabove, cocoa butter is composed of triglycerides. Complete hydrolysis thereof will hydrolyze all of the ester bonds to form a soap. Partially hydrolyzed cocoa butter is a product that contains partial hydrolysis of the triglycerides. Thus, partially hydrolyzed cocoa butter contains cocoa butter that has not reacted with the base as well as cocoa butter that as been hydrolyzed. As described hereinbelow, partially hydrolyzed cocoa butter is an emulsion. Thus, the term "partially hydrolyzed cocoa butter emulsion" refers to the emulsion product obtained from the partial hydrolysis of cocoa butter, i.e., oil in water emulsion. On the other hand, when reference is made to partially hydrolyzed cocoa butter, it refers to just the oil portion of the product.

Partially hydrolyzed cocoa butter emulsion is prepared by the procedures described in U.S. Pat. Nos. 3,856,936, 3,654, 327, 3,860,702 and 3,862,197, the contents of which are incorporated by reference. In accordance with the procedures described therein, the partially hydrolyzed cocoa butter emulsion is prepared by partially converting the cocoa butter to a soap by reacting a portion of the cocoa butter with an alkali base such as sodium hydroxide or potassium hydroxide in a manner insufficient to react all of the cocoa butter so that a part of the cocoa butter is unreacted and not converted to soap. Typically, excess base is utilized so that the degree of hydrolysis is controlled by the time of the reaction. The reaction is terminated by the addition of acid, such as mineral acid (e.g., hydrochloric acid) to neutralize the base. The resulting product is the partial hydrolyzed cocoa butter emulsion.

Typically, natural cocoa butter is melted by heating in hot water and saponified by the addition of a strong base, such as sodium hydroxide, potassium hydroxide, and the like, for example, sodium hydroxide at 6N concentration. The degree of hydrolysis is controlled by the time rate of reaction. The molar ratio of base to cocoa butter in the hydrolysis ranges from about 36:1 to about 6:1, but most preferably from about 12:1 to about 26:1. This mixture is heated, stirred continuously and held at the elevated temperature with stirring until hydrolysis is completed. Preferably, the temperature of the water ranges between 190°–210° C. In addition, the pH of the solution preferably ranges from about 10.0 to 12.00 and more preferably from 10.5 to 11.5, with pH equal to about 11.5 being the most preferred. The reaction mixture is held at these conditions until the desired amount of hydrolysis is competed. For example, the reaction mixture may undergo hydrolysis for about 5 minutes. This results in an incomplete saponification producing a mixture of unsaponified and saponified cocoa butter. When the desired hydrolysis is completed, the mixture is then acidified with acid such as hydrochloric acid, for example, 6N hydrochloric acid, accompanied by vigorous stirring. Preferably, the pH after initial addition of acid drops to about 2.5. At this point, the mixture is washed with water to remove salts, excess hydrochloric acid and glycerine, and the resulting product, a soft creamy mass, is recovered. The pH of the mixture is then raised to about 6.3–6.8 and most preferably to about 6.5.

The hydrolysis reactions by which the cocoa butter is first converted to soaps and then to free fatty acids are well known. They are the same reactions by which soaps and free fatty acids have been historically made from natural fats and oils. However, unlike conventional methods, there is only a partial hydrolysis rather than a complete hydrolysis conventionally carried out in soap making.

Alternatively, patially hydrolyzed cocoa butter emulsion is prepared by mixing cocoa butter with fully hydrolyzed cocoa butter or mixing cocoa butter with partially hydrolyzed cocoa butter using procedures described herein, or mixing fully hydrolyzed cocoa butter with partially hydrolyzed cocoa butter or combination thereof.

The resulting product is an oil in water emulsion which has a white creamy appearance. It is dispersible in water and will mix with water at any level ranging from 0% to 100% (w/w). It is preferred that the viscosity at 40° C. ranges from about 0.1 poise to about 1.0 poise, and even more preferred that at 40° C., the viscosity ranges from about 0.4 to 0.6 poise. In an even more preferred embodiment, a 30% emulsion has a viscosity at 40° C. of about 0.6 poise and a 10% emulsion has a viscosity at 40° C. of about 0.4 poise. The emulsion breaks at a temperature range from about 85° C. to about 100° C. In addition, in a preferred embodiment the slip melting point of the anhydrous partially hydrolyzed cocoa butter emulsion is about 43° C. The emulsion contains mostly water, ranging from about 70–90% water (w/w) and more preferably 70–85% water (w/w) and most preferably about 70% water (w/w). Thus, it is preferred that the amount of partially hydrolyzed cocoa butter present ranges from about 10 to about 30% (w/w), and more preferably 20–30% (w/w).

It is preferred that the percentage of cocoa butter that is hydrolyzed ranges from about 45% to about 70%. The free fatty acids found in the emulsion include mostly palmitic acid, stearic acid, and oleic acid. In the non-aqueous phase of the emulsion, the total amount of free fatty acids ranges from about 45% to about 65%, and more preferably from about 50% to about 60%, and most preferably about 56% (w/w). Of the amount of free fatty acid, the amount of oleic, stearic and palmitic acids are about the same. Preferably, the amount of palmitic acid in the non-aqueous phase of the emulsion ranges from about 10 to about 20% (w/w) and more preferably about 13% to about 17% and most preferably about 15.0% to about 15.5% (w/w). The amount of stearic acid in the non-aqueous phase of the emulsion ranges from about 15% to about 25% (w/w) and more preferably from about 18% to about 22% and most preferably from about 19.0% to about 19.5% (w/w). The oleic acid in the non-aqueous phase of the emulsion preferably ranges from about 17% to about 27% (w/w), and more preferably from about 19% to about 25% and most preferably from about 21.5% to about 22.5% (w/w).

The amount of triglycerides, i.e., unsaponified cocoa butter in the non-aqueous phase of the emulsion ranges from about 30% to about 55% (w/w) and more preferably from about 40% to about 50% (w/w) and most preferably about 48%.

The melted cocoa butter or partially hydrolyzed cocoa butter emulsion prepared in accordance with the procedure described hereinabove is mixed with the active drug, the retinoid, $\alpha$ or $\beta$-hydroxy carboxylic acid, etc.

Preferably, the active pharmacological agent in the pharmaceutical composition of the present invention is present in pharmaceutically effective amounts typically ranging from about 0.001% to about 80%, by weight based on the total weight of the composition and more preferably from 0.001% to about 50%, and even more preferably from about 0.01% to about 25% by weight. However, the effective amount of a specific pharmacological agent will vary in accordance with parameters well understood by the physician. These parameters include the condition being treated, the age, weight and physical condition of the subject, and, of course, the specific agent selected.

Thus, for example, the retinoids are more preferably present in the pharmaceutical composition of the present invention in amounts ranging from about 0.01% to about 1% (w/w). On the other hand, the steroids, including the corticosteroids and the testosterones, are more preferably present in the pharmaceutical composition of the present invention in amounts ranging from about 0.01 to about 10% (w/w). The hydroxy acids are preferably present in the pharmaceutical compositions of the present invention in amounts ranging from about 0.05 to about 20% (w/w), while vitamin D is more preferably present in the pharmaceutical composition of the present invention in amounts ranging from about 0.01% to about 2.5% (w/w).

In preparing the pharmacological agents of the present invention, the desired amount of medicinal agent is added to the cocoa butter in the melted state and mixed together. With respect to the pharmacological agents containing the partially hydrolyzed cocoa butter emulsion, the desired amount of medicinal agent is added to the partially hydrolyzed cocoa butter emulsion and mixed together.

Generally, for both cocoa butter and the hydrolyzed cocoa butter emulsion, they are present in the compositions of the present invention in penetration enhancement amounts. Typically, the concentration ranges from about 0.1% to about 100% (w/w), exclusive. The more preferred concentration of cocoa butter ranges from about 50% to about 99.99%, and the most preferred concentration ranges form 75% to about 99.99% (w/w). The more preferred concentration of partially hydrolyzed cocoa butter emulsion range from 50% to about 99.99%, while the most preferred range is from about 75% to about 99.99% (w/w).

The composition of the present invention may also contain other ingredients of the type commonly employed by those skilled in the art in formulating compositions for topical applications. These may include, for example, carrier, emollients, surfactants, emulsifying agents, auxiliary emulsifiers, emulsion stabilizer agents, antioxidants (e.g., butylated hydroxy toluene (BHT), butylated hydroxy anisole (BHA), ascorbic acid, propyl gallate, $\alpha$-tocopherol and the like), gelling agents (Carbopol 934 or Carbopol 940 and the like), thickening agents, preservatives, chelating agents, perfumes, fragrances and other penetration enhancer(s). Water may be additionally added to the pharmaceutical composition containing cocoa butter, but, in such a case, an emulsifying agent must additionally be present in the amounts indicated herein below.

The composition can be in the form of any suitable non-toxic or pharmaceutically acceptable topical carrier material or vehicle, such as a solution, suspension, emulsion, lotion, cream, gel, ointment, liposome, aerosol spray, polymeric gel, sol, catoplasm, plaster, patch, film or tape, all of which are well-known to those skilled in the art of topical pharmaceutical formulations.

These additional ingredients described hereinabove except for the emulsifier can vary from about 0.1 to 25% by weight of the composition and more particularly from about 0.1 to 15%.

An emulsifier is an optional ingredient in the pharmaceutical compositions containing the melted cocoa butter or the partially hydrolyzed cocoa butter emulsion. However, if the pharmaceutical composition containing melted cocoa butter contains a significant amount of water then, in this circumstance, an emulsifier is necessary. The amount of emulsifier used in the composition of the present invention, when present, will be an effective emulsifying amount. More particularly, the amount of emulsifier can vary from about 0.1 to 25% by weight of the composition and preferably from about 1 to 10% by weight.

The composition of the present invention may be used in an aerosol spray, in which a propellant is additionally added to the formulation. In this formulation, the propellant is usually present in amounts ranging from 0 to about 50% by weight, exclusive, and preferably from about 0 to 30%, exclusive. While any of the known propellants may be used in the compositions of the present invention, preferred propellants include the non-halogenated hydrocarbons, particularly the lower boiling hydrocarbons such as $C_3$–$C_6$ and branched chain hydrocarbons, e.g., propane, butane, isobutane and mixtures thereof. Other preferred propellants include the ethers such as dimethylether, hydrofluorocarbons and the compressed gases such as $N_2$ and $CO_2$.

The formulation of the present invention comprising the cocoa butter and/or hydrolyzed cocoa butter emulsion admixed with the medicinal agents have the same utility as the underlying medicinal agent; however, the present formulation is much more effective in its efficacy and ability to be absorbed through the skin than with other delivery agents commonly utilized. For example, retinoic acid, especially trans-retinoic acid and 13-cis-retinoic acid, such as retin-A (tretinoin) and accutane, are useful for treating acne. They also protect against photoaging, as described hereinabove. But the combination of cocoa butter or partially hydrolyzed cocoa butter emulsion with these retinoids, has the same utility as the individual retinoids, but is even more effective. For instance, cocoa butter as well as partially hydrolyzed cocoa butter emulsion was found to significantly increase the absorption of retinoic acids, e.g., retin-A or accutane, through the skin relative to agents currently available. For example, the inventors found that the average absorption of retinoic acids with both cocoa butter as well as partially hydrolyzed cocoa butter emulsion was found to be 16.5%, as compared with 1 to 5% from delivery agents now currently available. In addition, when the retinoic acids were admixed with the cocoa butter or partially hydrolyzed cocoa butter emulsion, in accordance with the present invention, the retinoic acids were able to sustain a longer absorption period than has been demonstrated with current retinoic acid formulations. Thus the present formulations are more effective in treating acne conditions and photoaging relative to the retinoic acid formulations currently used having the same concentrations of retinoic acid. In addition since more retinoic acids are being absorbed through the skin than with the commonly utilized formulations containing retinoic acids, much less of the retinoic acids are required to achieve an efficacious result. In other words, the retinoic acids utilized in combination with the cocoa butter or hydrolyzed cocoa butter emulsion are used in significantly lower concentrations than that used in current formulations and achieves the same efficacy as exhibited by current formulations with higher retinoic acid concentrations. Similarly, if the concentrations of retinoic acid used in the present invention are the same as that used in commonly utilized formulations, the present formulation is far more effective.

As another example, cocoa butter or partially hydrolyzed cocoa butter emulsion when combined with a glucocorticoid, such as a corticosteroid, e.g., triamcinolone acetonide, has the same utility as the underlying glucocorticoid. However, when the glucocorticoid is combined with the cocoa butter or hydrolyzed cocoa butter emulsion, the efficacy significantly increases since the presence of the cocoa butter or partially hydrolyzed cocoa butter emulsion significantly improves the amount of absorption compared with delivery agents presently available. In tests that were conducted, it was found that the average absorption of triamcinolone acetonide with cocoa butter or partially hydrolyzed cocoa butter was about 11%, which is significantly greater than the absorption of corticosteroid compounds (e.g., hydrocortisone, hydrocortisone acetate, cortisone, fluocinolone acetonide, and the like) which is in the range of about 1–3% of the dose.

Thus, cocoa butter or partially hydrolyzed cocoa butter emulsion when combined with medicinal agents such as steroids, retinoids, as well as with α- or β-hydroxycarboxylic acid or vitamin D, increases the efficacy thereof by topical application since it permits greater total and/or rate of absorption through the skin. Therefore, the use of cocoa butter or partially hydrolyzed cocoa butter emulsion in topical formulations is valuable to dermatologists for delivery of a medicinal agent to the treated area as the first mode of treatment for skin disease.

The present invention will now be described with reference to the examples which follow. It should be noted, however, that the present invention is not deemed to be limited only to these examples.

EXAMPLE 1

The procedure is for making partially hydrolyzed cocoa butter emulsion.

Pure cocoa butter was melted by heating to 190° F. Sufficient 6N NaOH was added to raise the pH of the mixture of 11.5. The temperature was raised to 210° C. as the mixture was stirred. The pH of the solution was 11.5 at the end of five minutes. The basic mixture was neutralized with sufficient 6N HCl until the pH became 2.5. The mixture was rinsed three times with 190° F. water. The pH was increased to 6.5 with the addition of 6N NaOH. An emulsion was formed at 190° F. and the water content was adjusted to the desired concentration.

The percent of $H_2O$ present in the product was 70% (w/w). The percent of individual free fatty acids including the sodium salts of the free fatty acids in the non-aqueous phase of the product was:

| | |
|---|---|
| Palmitic | 15.3% (w/w) |
| Stearic | 19.2% (w/w) |
| Oleic | 22.0% (w/w) |

Then, under these conditions, the total free fatty acids including the sodium salts was 56% (w/w) and the amount of triglycerides left in the non-aqueous phase of the emulsion was 48% (w/w).

EXAMPLE 2

Objective

The objective of this study was to measure the permeation of retinoic acid and triamcinolone acetonide through human skin in-vitro from two cocoa butter vehicles.

Material and Methods

A. Formulations

Two cocoa butter vehicles supplied by Hershey Foods Corporation were utilized: (1) pure cocoa butter and (2) partially hydrolyzed cocoa butter emulsion. Radioactive [11,12-$^3$H] [retinoic acid (NET 920, Lot 2930-067, specific activity 1 mCi/ml) and [6,7-$^3$H]-triamcinolone acetonide (NET 470, Lot 2904-170, specific activity 1 mCi/ml) were obtained from Dupont-New England Nuclear Corporation, Boston, Mass.

Each of the two cocoa butter vehicles was spiked separately with $^3$H-retinoic acid and $^3$H-Triamcinolone acetonide to give a total of four radioactive formulations for study. This was done by adding 25 µl (containing 25 µCi) of each tracer solution to approximately 1 gram of each vehicle and mixing with the tip of the dispensing micropipette. The pure cocoa butter vehicle was liquified by holding it under warm tap water prior to spiking. This was not done with the partially hydrolyzed cocoa butter emulsion. Neither formulation was used for three days after spiking to allow for diffusional mixing to take place. Final radioactive concentrations of each formulation were:

| | |
|---|---|
| 1. $^3$H-retinoic acid/emulsion | 49,239 dpm/mg |
| 2. $^3$H-retinoic acid/butter | 40,606 dpm/µl |
| 3. $^3$H-triamcinolone/emulsion | 55,295 dpm/mg |
| 4. $^3$H-triamcinolone/butter | 46,735 dpm/µl |

B. Skin Preparation

Human trunk skin without obvious signs of disease was used throughout. It was obtained within 24 hours of death, dermatomed to a thickness of approximately 0.25 mm, cryopreserved and sealed in water vapor-impermeable plastic bags. It was stored at −70° C. until the day of use then thawed by placing the bag in 37° C. water.

Skin from a single donor was cut into multiple sections large enough to fit on 0.8 cm$^2$ Franz cells. The dermal chamber was filled with isotonic saline, pH 7.4, into which a small magnetic stirring bar was placed. The epidermal chamber was left open to the ambient laboratory environment, approximately 22° C. and 40–60% RH. The cells were placed in a diffusion apparatus in which the dermal receptor solution was stirred magnetically at 600 RPM and its temperature maintained at 37° C.

To assure the integrity of each skin section, its permeability to tritiated water was determined before application of the test formulations. Following a brief (0.5–1 hour) equilibration period, 150 µl $^3$H$_2$O (specific activity 0.3 µCi/ml) was layered across the top of the skin section so that the entire exposed surface was covered. After 5 minutes the aqueous layer was removed and the surface of the skin carefully blotted dry. At t=0.5 hour the saline receptor phase was removed and analyzed for radioactive content by liquid scintillation counting. Skin specimens in which absorption of $^3$H$_2$O was less than 1.25 µl were considered acceptable.

C. Percutaneous Absorption

Following measurement of $^3$H$_2$O absorption, the receptor solution was changed several times to remove all traces of radioactivity, then replaced with phosphate-buffered saline containing 0.5% Volpo 20 (Croda Inc., New York, N.Y.) to increase its solubility to retinoic acid and triamcinolone acetonide. Subsequently, each test formulation was applied at a target dose of 10 mg (cream) or 10 µl (butter). The cream formulation (partially hydrolyzed cocoa butter emulsion) was applied from the smooth, rounded-tip of a glass rod, the exact amount determined by weighing the rod before and after application. The butter formulation (pure cocoa butter) was first liquified under warm tap water, allowed to cool to room temperature, then applied with a 10 µl positive displacement micropipette prior to resolidifying. At 4, 8, 12, 24, 36 and 48 hours the receptor solution was removed in its entirety, replaced with fresh solution, and a 1 ml aliquot taken and assayed for radioactive content by liquid scintillation counting.

D. Radioactive Assay

A 1 ml aliquot of each receptor sample containing $^3$H$_2$O, $^3$H-retinoic acid, or $^3$H-triamcinolone acetonide was placed in a 7 ml glass scintillation vial and gelled by the addition of 5 ml Opti-Fluor (Packard Instrument Co., Meriden, Conn.). These were counted in a Packard Tri-Carb Model 1900CA Liquid scintillation Analyzer equipped with internal standard and automatic quench correction.

E. Statistical Analysis

Each of the two cocoa butter vehicles, containing either $^3$H-retinoic acid or $^3$H-triamcinolone acetonide, were run simultaneously and on quadruplicate sections of skin from three separate donors. Two parameters were calculated: (1) rate of absorption and (2) total absorption.

The rate of absorption was calculated by taking the amount of tracer found in any receptor sample and dividing by the time interval (hours) over which that sample was collected. Flux data were expressed both as percent dose/hr and ng/cm$^2$/hr, the latter calculated on the basis of an assumed drug concentration of 0.1% for both retinoic acid and triamcinolone acetonide. (0.1% was chosen since this is a concentration common to many commercial formulations of both drugs.) Total absorption was calculated by summing the mount of tracer found in each of the six receptor samples taken over the 48-hour course of the experiment.

Results

A. Rate of Absorption

The data for retinoic acid and triamcinolone acetonide are summarized in Tables 1 and 2, respectively, hereinbelow:

TABLE 1

ABSORPTION OF RETINOIC ACID

Skin: 1A

| Butter Sample | A | B | D | E | Average | Mid-t |
|---|---|---|---|---|---|---|
| R1 | 36.55 | 48.20 | 39.43 | 51.22 | 43.85 | 2 |
| R2 | 30.62 | 41.05 | 31.94 | 34.16 | 34.44 | 6 |
| R3 | 23.55 | 28.39 | 24.05 | 29.61 | 26.40 | 10 |
| R4 | 14.13 | 23.33 | 15.22 | 18.56 | 17.81 | 18 |
| R5 | 16.12 | 19.00 | 18.23 | 16.25 | 17.40 | 30 |
| R6 | 15.54 | 17.94 | 14.86 | 24.92 | 18.31 | 42 |
| Penet | 729.80 | 954.98 | 769.08 | 941.38 | 848.81 | |
| % Abs | 14.59 | 19.10 | 15.38 | 18.82 | 16.97 | |

Skin: IIA

| Butter Sample | M | N | O | P | Average | Mid-t |
|---|---|---|---|---|---|---|
| R1 | 55.25 | 66.87 | 50.92 | 79.43 | 63.12 | 2 |
| R2 | 23.74 | 27.36 | 22.95 | 38.32 | 28.10 | 6 |
| R3 | 22.32 | 21.53 | 20.69 | 34.12 | 24.67 | 10 |
| R4 | 18.11 | 20.56 | 20.18 | 33.78 | 23.16 | 18 |
| R5 | 11.93 | 15.30 | 12.34 | 23.05 | 15.66 | 30 |
| R6 | 11.83 | 16.34 | 13.15 | 24.58 | 16.48 | 42 |
| Penet | 725.19 | 871.67 | 741.10 | 1267.53 | 901.37 | |
| % Abs | 14.50 | 17.43 | 14.82 | 25.35 | 18.02 | |

TABLE 1-continued

ABSORPTION OF RETINOIC ACID

Skin: IIIA

| Butter Sample | MW | NN | OO | PP | Average | Mid-t |
|---|---|---|---|---|---|---|
| R1 | 40.64 | 39.67 | 51.71 | 75.03 | 51.76 | 2 |
| R2 | 18.78 | 19.13 | 30.85 | 31.37 | 25.03 | 6 |
| R3 | 16.59 | 15.24 | 17.69 | 25.75 | 18.82 | 10 |
| R4 | 15.63 | 14.10 | 16.64 | 23.97 | 17.59 | 18 |
| R5 | 8.38 | 9.60 | 10.78 | 16.34 | 11.28 | 30 |
| R6 | 8.20 | 9.16 | 10.53 | 14.03 | 10.48 | 42 |
| Penet | 552.40 | 552.46 | 685.17 | 944.68 | 683.68 | |
| % Abs | 11.05 | 11.05 | 13.70 | 18.89 | 13.67 | |

Skin: IB

| Cream Sample | G | H | I | J | Average | Mid-t |
|---|---|---|---|---|---|---|
| R1 | 40.91 | 36.94 | 38.12 | 45.28 | 40.32 | 2 |
| R2 | 34.47 | 29.41 | 35.40 | 30.68 | 32.49 | 6 |
| R3 | 23.20 | 19.99 | 20.80 | 24.15 | 22.04 | 10 |
| R4 | 17.83 | 16.44 | 14.68 | 15.42 | 16.09 | 18 |
| R5 | 14.89 | 15.68 | 17.30 | 17.77 | 16.41 | 30 |
| R6 | 20.33 | 14.24 | 14.46 | 17.62 | 16.62 | 42 |
| Penet | 824.73 | 721.36 | 745.68 | 808.17 | 774.99 | |
| % Abs | 14.03 | 14.76 | 13.59 | 17.11 | 14.87 | |

Skin: IIB

| Cream Sample | O | R | S | T | Average | Mid-t |
|---|---|---|---|---|---|---|
| R1 | 74.50 | 68.54 | 46.23 | 49.65 | 59.73 | 2 |
| R2 | 38.08 | 39.69 | 21.10 | 17.02 | 28.97 | 6 |
| R3 | 28.97 | 25.18 | 16.74 | 15.77 | 21.67 | 10 |
| R4 | 27.53 | 24.05 | 12.20 | 11.56 | 18.83 | 18 |
| R5 | 15.95 | 14.81 | 8.32 | 7.95 | 11.76 | 30 |
| R6 | 16.38 | 15.16 | 8.78 | 7.68 | 12.00 | 42 |
| Penet | 1027.61 | 945.49 | 550.30 | 524.77 | 762.04 | |
| % Abs | 17.20 | 15.81 | 13.56 | 15.67 | 15.56 | |

Skin: IIIB

| Cream Sample | OO | RR | SS | XX | Average | Mid-t |
|---|---|---|---|---|---|---|
| R1 | 16.18 | 50.09 | 69.86 | 77.41 | 65.14 | 2 |
| R2 | 32.81 | 20.51 | 28.54 | 34.97 | 29.21 | 6 |
| R3 | 27.41 | 19.26 | 26.16 | 30.74 | 25.89 | 10 |
| R4 | 26.23 | 18.49 | 25.34 | 30.20 | 25.07 | 18 |
| R5 | 15.24 | 11.88 | 12.50 | 19.16 | 14.70 | 30 |
| R6 | 13.21 | 9.49 | 10.20 | 14.22 | 11.78 | 42 |
| Penet | 919.75 | 670.20 | 859.80 | 1068.35 | 879.52 | |
| % Abs | 21.00 | 18.37 | 18.57 | 20.67 | 19.65 | |

Overall Summary: Hersheys-Retinoic Acid

| Butter Sample | Skin:I | Skin:II | Skin:III | Average | SE | Mid-t |
|---|---|---|---|---|---|---|
| R1 | 51.76 | 63.12 | 43.85 | 52.91 | 5.59 | 2 |
| R2 | 25.03 | 28.10 | 34.44 | 29.19 | 2.77 | 6 |
| R3 | 18.82 | 24.67 | 26.40 | 23.30 | 2.29 | 10 |
| R4 | 17.59 | 23.16 | 17.81 | 19.52 | 1.82 | 18 |
| R5 | 11.28 | 15.66 | 17.40 | 14.78 | 1.82 | 30 |
| R6 | 10.48 | 16.48 | 18.31 | 15.09 | 2.36 | 42 |
| Total Penentration | 683.68 | 901.37 | 848.81 | 811.29 | 65.58 | |
| % Absorbedn | 13.67 | 18.02 | 16.97 | 16.22 | 1.31 | |
| | 4 | 4 | 4 | | | |

| Cream Sample | Skin:I | Skin:II | Skin:III | Average | SE | Mid-t |
|---|---|---|---|---|---|---|
| R1 | 65.14 | 59.73 | 40.32 | 55.06 | 7.54 | 2 |
| R2 | 29.21 | 28.97 | 32.49 | 30.22 | 1.13 | 6 |
| R3 | 25.89 | 21.67 | 22.04 | 23.20 | 1.35 | 10 |
| R4 | 25.07 | 18.83 | 16.09 | 20.00 | 2.66 | 18 |
| R5 | 14.70 | 11.76 | 16.41 | 14.29 | 1.36 | 30 |
| R6 | 11.78 | 12.00 | 16.62 | 13.47 | 1.58 | 42 |
| Total Penentration | 879.52 | 762.04 | 774.99 | 805.52 | 37.19 | |
| % Absorbedn | 19.65 | 15.56 | 14.87 | 16.69 | 1.49 | |
| | 4 | 4 | 4 | | | |

TABLE 2

ABSORPTION OF TRIAMINOLONE ACETONIDE

Skin: IVA

| Cream Sample | MM | NN | OO | PP | Average | Mid-t |
|---|---|---|---|---|---|---|
| R1 | 3.04 | 1.67 | 5.26 | 1.52 | 2.87 | 2.00 |
| R2 | 2.71 | 1.70 | 5.09 | 0.99 | 2.62 | 6.00 |
| R3 | 3.36 | 3.23 | 5.64 | 0.96 | 3.30 | 10.00 |
| R4 | 5.74 | 12.44 | 6.13 | 2.07 | 6.60 | 18.00 |
| R5 | 7.24 | 17.67 | 6.59 | 3.75 | 8.81 | 30.00 |
| R6 | 10.49 | 37.33 | 7.93 | 5.35 | 15.28 | 42.00 |
| Penet | 254.48 | 668.59 | 249.45 | 118.36 | 322.72 | |
| % Abs | 2.49 | 6.22 | 2.57 | 1.23 | 3.13 | |

Skin: VA

| Cream Sample | M | N | O | P | Average | Mid-t |
|---|---|---|---|---|---|---|
| R1 | 18.29 | 17.50 | 18.71 | 12.90 | 16.85 | 2.00 |
| R2 | 48.35 | 46.20 | 51.20 | 37.35 | 45.76 | 6.00 |
| R3 | 59.17 | 56.60 | 68.40 | 55.15 | 59.83 | 10.00 |
| R4 | 63.18 | 60.43 | 79.96 | 72.84 | 69.10 | 18.00 |
| R5 | 73.13 | 69.96 | 81.15 | 70.51 | 73.68 | 30.00 |
| R6 | 83.06 | 70.37 | 91.88 | 81.89 | 81.80 | 42.00 |
| Penet | 2508.36 | 2312.05 | 2871.31 | 2499.51 | 2547.81 | |
| % Abs | 19.85 | 17.85 | 23.91 | 21.77 | 20.84 | |

Skin: VIA

| Cream Sample | OO | SS | TT | UU | Average | Mid-t |
|---|---|---|---|---|---|---|
| R1 | 4.30 | 2.33 | 15.97 | 3.83 | 6.61 | 2.00 |
| R2 | 15.63 | 12.00 | 13.68 | 13.89 | 13.80 | 6.00 |
| R3 | 21.00 | 18.75 | 20.37 | 22.71 | 20.71 | 10.00 |
| R4 | 26.40 | 25.54 | 27.04 | 31.56 | 27.64 | 18.00 |
| R5 | 30.37 | 30.85 | 35.59 | 41.22 | 34.51 | 30.00 |
| R6 | 28.80 | 30.03 | 32.01 | 46.16 | 34.12 | 42.00 |
| Penet | 947.51 | 935.57 | 1068.65 | 1271.22 | 1055.74 | |
| % Abs | 9.37 | 8.49 | 9.22 | 13.72 | 10.20 | |

Skin: IVB

| Butter SE | OO | SS | TT | VV | Average | Mid-t |
|---|---|---|---|---|---|---|
| R1 | 4.39 | 1.60 | 4.85 | 2.94 | 3.45 | 2.00 |
| R2 | 2.11 | 1.67 | 4.38 | 1.62 | 2.45 | 6.00 |
| R3 | 4.10 | 1.98 | 3.21 | 1.85 | 2.79 | 10.00 |
| R4 | 10.64 | 4.64 | 5.65 | 6.96 | 6.97 | 18.00 |
| R5 | 16.77 | 7.47 | 7.89 | 11.61 | 10.93 | 30.00 |
| R6 | 23.72 | 12.43 | 12.16 | 19.97 | 17.07 | 42.00 |
| Penet | 524.71 | 252.43 | 268.51 | 390.54 | 363.55 | |
| % Abs | 5.24 | 2.52 | 2.86 | 3.90 | 3.63 | |

TABLE 2-continued

ABSORPTION OF TRIAMINOLONE ACETONIDE

Skin: VB

| Butter Sample | O | R | S | T | Average | Mid-t |
|---|---|---|---|---|---|---|
| R1 | 5.03 | 5.86 | 13.93 | 14.30 | 9.78 | 2.00 |
| R2 | 22.20 | 27.03 | 27.00 | 20.15 | 24.10 | 6.00 |
| R3 | 39.10 | 54.60 | 49.52 | 41.58 | 46.20 | 10.00 |
| R4 | 41.81 | 61.91 | 60.58 | 63.34 | 56.91 | 18.00 |
| R5 | 44.77 | 55.96 | 68.48 | 56.67 | 56.47 | 30.00 |
| R6 | 48.08 | 65.20 | 60.71 | 62.32 | 59.08 | 42.00 |
| Penet | 1505.05 | 2037.47 | 2111.25 | 1993.70 | 1911.87 | |
| % Abs | 15.04 | 20.36 | 21.10 | 19.92 | 19.10 | |

Skin: VIB

| Butter Sample | MM | NN | OO | PP | Average | Mid-t |
|---|---|---|---|---|---|---|
| R1 | 10.13 | 6.97 | 3.85 | 4.31 | 6.32 | 2.00 |
| R2 | 20.01 | 6.24 | 7.04 | 9.05 | 10.59 | 6.00 |
| R3 | 31.25 | 11.42 | 13.09 | 17.61 | 18.34 | 10.00 |
| R4 | 42.50 | 16.59 | 19.25 | 21.60 | 24.98 | 18.00 |
| R5 | 44.03 | 24.96 | 28.20 | 30.50 | 31.92 | 30.00 |
| R6 | 49.91 | 30.50 | 30.09 | 34.64 | 36.29 | 42.00 |
| Penet | 1506.22 | 770.57 | 821.16 | 931.82 | 1077.44 | |
| % Abs | 15.05 | 7.70 | 8.21 | 9.31 | 10.07 | |

Overall Summary: Hersheys-Triamcinalone

| Butter Sample | Skin:IV | Skin:V | Skin:VI | Average | SE | Mid-t |
|---|---|---|---|---|---|---|
| R1 | 3.45 | 9.78 | 6.32 | 6.52 | 1.83 | 2 |
| R2 | 2.45 | 24.10 | 10.59 | 12.38 | 6.31 | 6 |
| R3 | 2.79 | 46.20 | 18.34 | 22.44 | 12.70 | 10 |
| R4 | 6.97 | 56.91 | 24.98 | 29.62 | 14.60 | 18 |
| R5 | 10.93 | 56.47 | 31.92 | 33.11 | 13.16 | 30 |
| R6 | 17.07 | 59.08 | 36.29 | 37.48 | 12.14 | 42 |
| Total Penentration | 363.55 | 1911.87 | 1007.44 | 1094.29 | 449.07 | |
| % Absorbed | 3.63 | 19.10 | 10.07 | 10.93 | 4.49 | |
| n | 4 | 4 | 4 | | | |

| Cream Sample | Skin:IV | Skin:V | Skin:VI | Average | SE | Mid-t |
|---|---|---|---|---|---|---|
| R1 | 2.87 | 16.85 | 6.61 | 8.78 | 4.18 | 2 |
| R2 | 2.62 | 45.76 | 13.80 | 20.73 | 12.93 | 6 |
| R3 | 3.30 | 59.83 | 20.71 | 27.95 | 16.72 | 10 |
| R4 | 6.60 | 69.10 | 27.64 | 34.45 | 18.36 | 18 |
| R5 | 8.81 | 73.68 | 34.51 | 39.00 | 18.86 | 30 |
| R6 | 15.28 | 81.80 | 34.12 | 43.73 | 19.80 | 42 |
| Total Penentration | 322.72 | 2574.81 | 1055.74 | 1308.76 | 654.67 | |
| % Absorbed | 3.13 | 20.84 | 10.20 | 11.39 | 5.15 | |
| n | 4 | 4 | 4 | | | |

Figure 2:
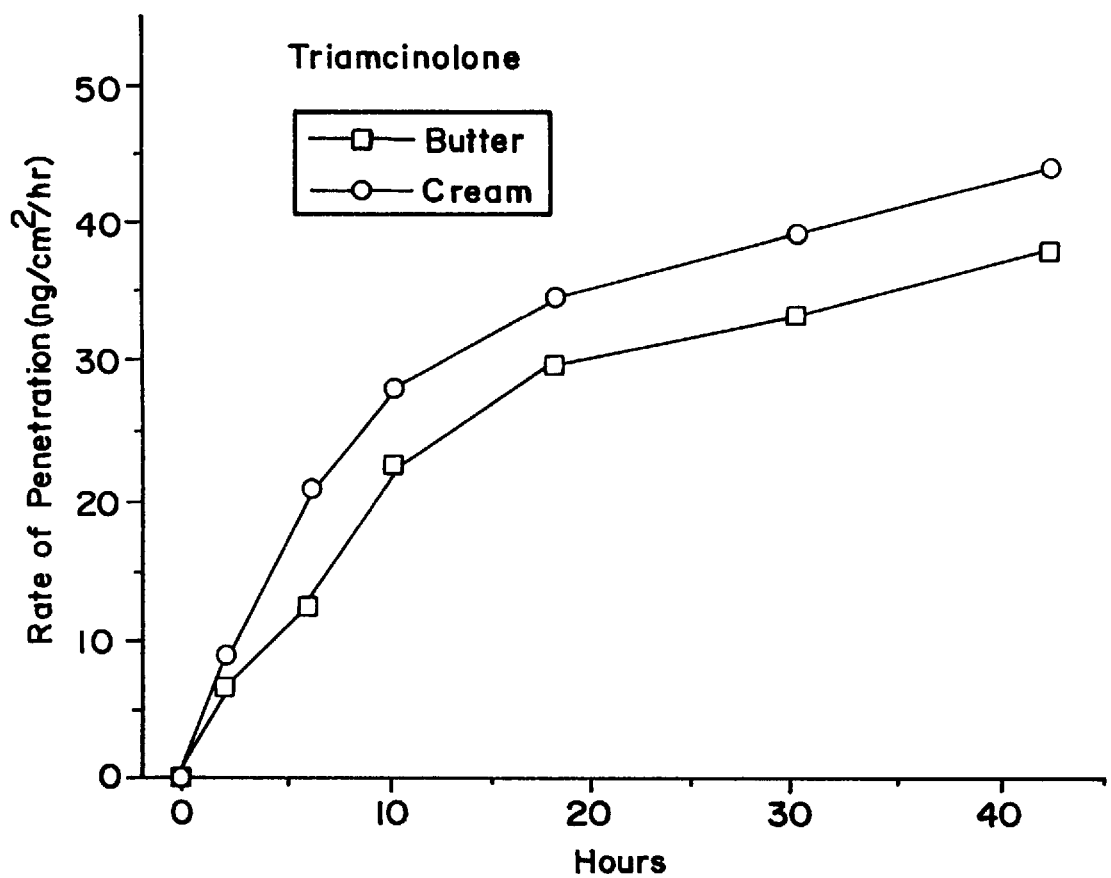
FIG. 2 is a rate profile of the absorption of triamcinolone through human trunk skin using cocoa butter and partially hydrolyzed cocoa butter emulsion (cream)

The rate of absorption profiles for retinoic acid and triamcinolone acetonide from both formulations are presented in FIGS. 1 and 2.

The rate of absorption profile of retinoic acid from both cocoa butter formulations is similar to that seen with other formulations of retinoic acid. There is an initial peak in the rate followed by a decay to what appears to be a steady state of approximately 15 ng/cm$^2$/hr. However, when the retinoic acid is admixed with either cocoa butter or partially hydrolyzed cocoa butter emulsion this value is higher than generally seen with other retinoic acid formulations. Both formulations give similar rates of absorption.

The rate of absorption profile of triamcinolone acetonide from both cocoa butter formulations is similar to that observed with other corticosteroids. Absorption begins very slowly and then rises to a steady state after 10–20 hours. In this case a steady state is not seen, rather, absorption continues to increase at a slow rate. The cream formulation gives a slightly higher rate of absorption than the butter in this case.

B. Total Absorption

Figure 3:
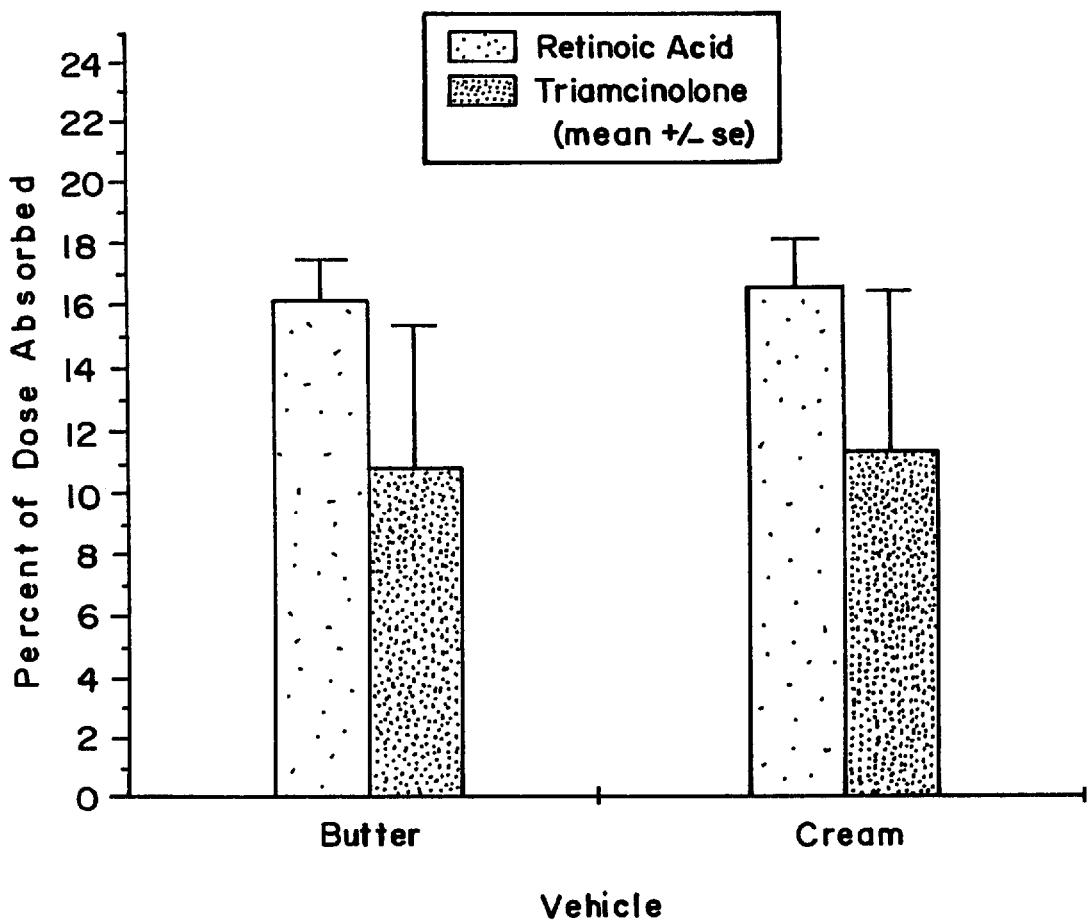
FIG. 3 is a graphical depiction of the total absorption expressed as percent of applied dose of retinoic acid and triamcinolone through human trunk skin using cocoa butter or partially hydrolyzed cocoa butter emulsion a the penetration enhancer.

Total absorption, expressed as percent of applied dose, is presented in FIG. 3. A summary of the data from which the figure was made is given in Tables 1 and 2. Total absorption of retinoic acid averages 16.2% and 16.7% for the butter and cream formulations, respectively. Total absorption of triamcinolone acetonide averaged 10.9% and 11.4% for the butter and cream formulations, respectively.

Thus, two major conclusions can be drawn form these experiments: (1) there is no appreciable difference between the partially hydrolyzed cocoa butter emulsion and pure cocoa butter with respect to their ability to serve as vehicles for the delivery of either retinoic acid or triamcinolone acetonide, (2) both vehicles lead to the attainment of relatively high flux rates of both retinoic acid and triamcinolone acetonide.

It has been found that total absorption of retinoic acid in the currently available formulations through trunk skin to generally be in the range of 1–5% of the dose. For example, a study of 7 experimental formulations gave the results shown in the table below. Similar results have been obtained with the commercial retinoic acid formulations (Retin-A).

Total Retinoic Acid Absorption at 48 Hours
(% of applied dose)

| Expt. | A | B | C | D | E | F | G |
|---|---|---|---|---|---|---|---|
| 1 | 1.16 | 0.45 | 1.02 | 0.81 | 1.71 | 0.63 | 0.96 |
| 2 | 3.23 | 1.76 | 6.03 | 1.76 | 5.18 | 2.01 | 5.46 |
| 3 | 2.37 | 0.99 | 1.73 | 1.02 | 2.32 | 0.97 | 2.15 |
| 4 | 1.40 | 0.72 | 1.45 | 0.82 | 1.93 | 1.43 | 0.86 |
| Mean I* | 2.04 | 0.98 | 2.56 | 1.10 | 2.79 | 1.26 | 2.36 |
| SEM | 0.48 | 0.28 | 1.17 | 0.22 | 0.81 | 0.30 | 1.07 |
| Mean II** | 1.64 | 0.72 | 1.40 | 0.88 | 1.99 | 1.01 | 1.32 |
| SEM | 0.37 | 0.16 | 0.21 | 0.07 | 0.18 | 0.23 | 0.41 |

*Mean I is the mean of all 4 experiments.
**Mean II excludes experiment #2.
SEM: Standard Error of Mean In contrast, the average absorption or retinoic acid when cocoa butter or partially hydrolyzed cocoa butter is used was found to be 16.5%.

Data in the published literature confirm that closely related corticosteroid compounds (hydrocortisone, hydrocortisone acetate, cortisone, fluocinolone acetonide) are also poorly absorbed through the skin, usually in the range of 1–3% of the dose. For example, see the data in the table below which is taken from Feldmann and Maibach (J. Invest. Dermatol., 52:89, 1969).

ABSORPTION AFTER TOPICAL ADMINISTRATION

| | Time (hrs) | Absorption Rate (% hr) | | | | | Total Absorption | | |
|---|---|---|---|---|---|---|---|---|---|
| Steroids | 0–12 | 12–24 | 24–48 | 48–72 | 72–96 | 96–120 | T of above | S.D. | No. Subjects |
| Hydrocortisone | .005 | .023 | .019 | .018 | .016 | .010 | 1.87 | 1.50 | 15 |
| Hydrocortisone Acetate | .020 | .089 | .032 | .024 | .015 | .008 | 2.55 | 1.80 | 6 |
| Cortisone | .015 | .037 | .039 | .036 | .032 | .024 | 3.38 | 1.64 | 7 |
| Corticosterone | .013 | .065 | .139 | .070 | .050 | .039 | 8.78 | 5.35 | 6 |
| 17-OII DOC | .041 | .101 | .084 | .076 | .062 | .065 | 8.41 | 4.28 | 5 |
| Desoxycorticosterone | .197 | .313 | .143 | .069 | .035 | .020 | 12.55 | 8.53 | 6 |
| 17-OII Progesterone | .042 | .120 | .213 | .211 | .078 | .031 | 14.76 | 11.35 | 7 |
| Progesterone | .208 | .264 | .135 | .045 | .024 | .011 | 10.81 | 5.78 | 6 |
| Flucinoione Acetonide | .002 | .011 | .012 | .016 | .008 | .005 | 1.34 | 1.05 | 9 |
| Dexamethasone | .005 | .003 | .004 | .003 | .002 | .002 | .40 | .23 | 3 |
| Estradiol | .008 | .056 | .099 | .101 | .107 | .103 | 10.62 | 4.86 | 3 |
| Testosterone | .147 | .364 | .156 | .066 | .036 | .018 | 13.24 | 3.04 | 17 |
| Testosterone Acetate | .103 | .133 | .048 | .015 | .007 | .004 | 4.62 | 2.28 | 6 |
| Testosterone Propionate | .061 | .096 | .035 | .015 | .009 | .005 | 3.44 | 1.03 | 9 |
| Dehydroepiandrosterone | .265 | .446 | .249 | .091 | .046 | .028 | 18.45 | 7.71 | 6 |
| Androstenedione | .183 | .334 | .155 | .076 | .043 | .028 | 13.47 | 5.56 | 11 |

In contrast, as indicated hereinabove, the average absorption of corticosteroid compounds found by the present inventors when cocoa butter or partially hydrolyzed cocoa butter emulsion was used was approximately 11%.

Thus, the two cocoa butter vehicles have enhancing capabilities and increase the absorbance of substances through the skin relative to other vehicles used for topical applications. Furthermore, the present combination of cocoa butter or partially hydrolyzed cocoa butter emulsion with retinoids, α- or β-hydroxycarboxylic acid, vitamin D or steroids, including corticosteroids and testosterones, improve the efficacy of the medicaments compared to current formulations containing same.

The above preferred embodiments and examples are given to illustrate the scope and spirit of the present invention. These embodiments and examples will make apparent to those skilled in the art other embodiments and examples. These other embodiments and examples are also within the contemplation of the present invention. Therefore the present invention should only be limited by the appended claims.

What is claimed is:

1. A topical composition for enhancing the skin penetration of a pharmaceutically active agent in a mammal, wherein the pharmaceutically active agent is a retinoid, steroid, Vitamin D or α- or β-hydroxy carboxylic acid comprising a safe and pharmaceutically effective amount of said pharmaceutically active agent admixed with a penetration enhancing effective amount of a partially hydrolyzed cocoa butter emulsion and a pharmaceutically carrier thereof, wherein said partially hydrolyzed cocoa butter emulsion comprises water, fatty acid and unsaponified cocoa butter, the partially hydrolyzed cocoa butter emulsion contains an aqueous and non-aqueous phase, said fatty acid comprises palmitic acid, stearic acid, and oleic acid, the amount of palmitic acid present in the non-aqueous phase of the emulsion ranges from about 10% to about 20% by weight, the amount of stearic acid in the non-aqueous phase of the emulsion ranges from about 15% to about 25% by weight and the amount of oleic acid in the non-aqueous phase ranges from about 17% to about 27% by weight.

2. The topical composition according to claim 1 wherein the amount of water present in the partially hydrolyzed cocoa butter emulsion ranges from about 70%–90% by weight.

3. The topical composition according to claim 2 wherein the amount of water present in the partial hydrolyzed cocoa butter ranges from about 70–85% by weight.

4. The topical composition according to claim 3 wherein the amount of water present in the partially hydrolyzed cocoa butter emulsion is about 70% by weight.

5. The topical composition according to claim 1 wherein the amount of unsaponified cocoa butter in the non-aqueous phase of the emulsion ranges from about 30% to about 55% by weight.

6. The topical composition according to claim 5 wherein the amount of unsaponified cocoa butter present in the non-aqueous phase of the emulsion ranges from about 40% to about 50% by weight.

7. The topical composition according to claim 1 wherein the amount of palmitic acid present in the non-aqueous phase of the emulsion ranges from about 13% to about 17% by weight.

8. The topical composition according to claim 7 wherein the amount of palmitic acid present in the non-aqueous phase of the emulsion ranges from about 15.0% to about 15.5% by weight.

9. The topical composition according to claim 1 wherein the amount of stearic acid present in the non-aqueous phase of the emulsion ranges from about 18% to about 22% by weight.

10. The topical composition according to claim 9 wherein the amount of stearic acid present in the non-aqueous phase of the emulsion ranges from about 19.0% to about 19.5% by weight.

11. The topical composition according to claim 1 wherein the amount of oleic acid present in the in the non-aqueous phase of the emulsion ranges from about 19.0% to about 25% by weight.

12. The topical composition according to claim 11 wherein the amount of oleic acid present in the non-aqueous phrase of the emulsion ranges from about 21.5% to about 22.5% by weight.

13. The topical composition according to claim 1 wherein the amount of palmitic acid, stearic acid and oleic acid present in the non-aqueous phase of the emulsion ranges from about 13% to about 17% by weight, about 18% to about 22% by weight and about 19% to about 25% by weight, respectively.

14. The topical composition according to claim 13 wherein the amount of unsaponified cocoa butter present in the non-aqueous phase ranges from about 40% to about 50% by weight.

15. The topical composition according to claim 1 wherein the pharmaceutical active agent is present in the topical composition in amounts ranging from about 0.001% to about 80% by weight.

16. The topical composition according to claim 15 wherein the pharmaceutically active agent is present in the topical composition amounts ranging from about 0.001% to about 50% by weight.

17. The topical composition according to claim 16 wherein the pharmaceutically active agent is present in the topical composition in amounts ranging from about 0.01% to about 25% by weight.

18. The topical composition according to claim 1 wherein the amount of palmitic acid and stearic acid present in the non-aqueous phase of the emulsion ranges from about 13% to about 17% by weight and about 18% to about 22% by weight, respectively.

19. The topical composition according to claim 18 wherein the amount of unsaponified cocoa butter present in the non-aqueous phase ranges from about 40% to about 50% by weight.

20. The topical composition according to claim 1 wherein the amount of palmitic acid and oleic acid present in the non-aqueous phase of the emulsion ranges from about 13% to about 17% by weight and about 19% to about 25% by weight, respectively.

21. The topical composition according to claim 20 wherein the amount of unsaponified cocoa butter present in the non-aqueous phase ranges from about 40% to about 50% by weight.

22. The topical composition according to claim 1 wherein the amount of stearic acid and oleic acid present in the non-aqueous phase of the emulsion ranges from about 18% to about 22% by weight and about 19% to about 25% by weight, respectively.

23. The topical composition according to claim 22 wherein the amount of unsaponified cocoa butter present in the non-aqueous phase ranges from about 40% to about 50% by weight.

24. A topical composition for enhancing the skin penetration of a pharmaceutically active agent in a mammal, wherein the pharmaceutically active agent is a retinoid, steroid, vitamin D or α- or β-hydroxy carboxylic acid comprising a safe and effective amount of said pharmaceutically active agent admixed with a penetration enhancing effective amount of a partially hydrolyzed cocoa butter emulsion, wherein said partially hydrolyzed cocoa butter emulsion comprises water, stearic acid, palmitic acid, oleic acid and unsaponified cocoa butter and wherein the amount of water present in the partially hydrolyzed cocoa butter emulsion ranges from about 70%–90% by weight.

25. The topical composition according to claim 24 wherein the amount of water present in the partially hydrolyzed cocoa butter emulsion ranges from about 70%–85% by weight.

26. The topical composition according to claim 25 wherein the amount of water present in the partially hydrolyzed cocoa butter emulsion is about 70% by weight.

27. The topical composition according to claim 24 wherein the palmitic acid is present in the non-aqueous phase thereof and wherein the amount of palmitic present in the non-aqueous phase ranges from about 10% to about 20% by weight.

28. The topical composition according to claim 24 wherein the stearic acid is present in the non-aqueous phase thereof and wherein the amount of stearic acid present in the non-aqueous phase ranges from about 15% to about 25% by weight.

29. The topical composition according to claim 24 wherein the oleic acid is present in the non-aqueous phase thereof and wherein the amount of oleic acid present in the non-aqueous phase ranges from about 17% to about 27% by weight.

30. The topical composition according to claim 24 wherein the unsaponified cocoa butter is present in the non-aqueous phase and the amount of unsaponified cocoa butter in the non-aqueous phase ranges from about 30% to about 55% by weight.

31. A topical composition for enhancing the skin penetration of a pharmaceutical active agent in a mammal, wherein the pharmaceutically active agent is a retinoid, steroid, Vitamin D or α- or β-hydroxy carboxylic acid comprising a safe and effective amount of said pharmaceutically active agent admixed with a penetration enhancing effective amount of a partially hydrolyzed cocoa butter emulsion and a pharmaceutical carrier therefor, wherein said partially hydrolyzed cocoa butter emulsion contains in the non-aqueous portion thereof about 4 to about 6% stearic acid (w/w), about 4.5% to about 6.5% oleic acid (w/w) and about 10 to about 15% triglyceride (w/w).

* * * * *

UNITED STATES PATENT AND TRADEMARK OFFICE
CERTIFICATE OF CORRECTION

PATENT NO. : 5,849,729
DATED : December 15, 1998
INVENTOR(S) : Barry L. Zoumas, et al.

It is certified that error appears in the above-identified patent and that said Letters Patent are hereby corrected as shown below:

Column 10, Line 17: "hydrolyed" should read --hydrolyzed--

Column 11, Line 17: "patially" should read --partially--

Column 18, Line 20: "triaminolone" should read --triamcinolone--

Column 19, Line 28: "triamcinalone" should read --triamcinolone--

Column 20, Line 23: "form" should read --from--

Column 21, Line 15: "flucinoine" should read --fluocinolone--

Column 22, Line 57, Claim 11: "in the in the" should read --in the--

Column 22, Line 62, Claim 12: "phrase" should read --phase--

Signed and Sealed this

Twenty-ninth Day of May, 2001

Attest:

NICHOLAS P. GODICI

*Attesting Officer*     *Acting Director of the United States Patent and Trademark Office*